(12) United States Patent
Kosaka et al.

(10) Patent No.: US 7,615,725 B2
(45) Date of Patent: Nov. 10, 2009

(54) HEATER CONTROLLING APPARATUS FOR GAS SENSOR

(75) Inventors: Yuji Kosaka, Obu (JP); Shuichi Nakano, Kariya (JP)

(73) Assignee: DENSO Corporation, Kariya (JP)

( * ) Notice: Subject to any disclaimer, the term of this patent is extended or adjusted under 35 U.S.C. 154(b) by 0 days.

(21) Appl. No.: 11/648,575

(22) Filed: Jan. 3, 2007

(65) Prior Publication Data

US 2007/0158333 A1     Jul. 12, 2007

(30) Foreign Application Priority Data

Jan. 10, 2006    (JP)   ............... 2006-002601

(51) Int. Cl.
*H05B 1/02*      (2006.01)

(52) U.S. Cl. ................ 219/483; 219/492; 219/497; 219/205

(58) Field of Classification Search ........... 219/492, 219/494, 497, 501, 505, 202, 205
See application file for complete search history.

(56) References Cited

U.S. PATENT DOCUMENTS

| 5,036,820 | A | * | 8/1991 | Fujimoto et al. | ............. 123/686 |
| 5,053,968 | A | * | 10/1991 | Uchinami | .................... 701/104 |
| 5,353,775 | A | * | 10/1994 | Yamashita et al. | ........... 123/686 |
| 5,616,835 | A | * | 4/1997 | Schnaibel et al. | ........... 73/117.2 |
| 5,656,190 | A | * | 8/1997 | Aoki | ........................... 219/505 |
| 6,192,678 | B1 | * | 2/2001 | Tachibana | .................... 60/289 |
| 6,781,098 | B2 | | 8/2004 | Toyoda | |
| 2003/0150209 | A1 | * | 8/2003 | Schnaibel et al. | ............. 60/285 |

* cited by examiner

*Primary Examiner*—Mark H Paschall
(74) *Attorney, Agent, or Firm*—Nixon & Vanderhye P.C.

(57) ABSTRACT

A heater controlling apparatus for controlling a heater that heats a sensing element of a gas sensor provided in an exhaust system of a diesel engine includes a device that changes a reference condition for controlling the heater after a start of the engine in a first operation based on an operational state before a stop of the engine in a second operation, which precedes the first operation.

22 Claims, 8 Drawing Sheets

HEATER CONTROLLING APPARATUS FOR GAS SENSOR

CROSS REFERENCE TO RELATED APPLICATION

This application is based on and incorporates herein by reference Japanese Patent Application No. 2006-2601 filed on Jan. 10, 2006.

BACKGROUND OF THE INVENTION

1. Field of the Invention

The present invention relates to a heater controlling apparatus for controlling a gas sensor heater of a gas sensor, which heats a sensing element of a gas sensor provided in an exhaust system of a diesel engine.

2. Description of Related Art

Due to strengthening a regulation of exhaust gas, an air fuel ratio control in a vehicle engine has become more important. Thus, in order to perform a feedback control of the air fuel ratio, a gas sensor is provided in an exhaust gas system of the engine to measure an oxygen concentration in the exhaust gas. When the gas sensor is used, a sensing element needs to be heated to an appropriate temperature by a heater in order to activate the sensing element. However, when the sensing element is heated by energizing the heater while water exists in the exhaust system (exhaust pipe) upstream of the gas sensor, the water may attach a surface of the sensing element and the element may be disadvantageously broken.

Thus, in general, a temperature of a wall of the exhaust pipe is assumed based on the exhaust temperature and on an engine coolant temperature, and then it is determined whether the water exists or not based on the wall temperature. When the wall temperature becomes a temperature, at which a heater energization can be made, the heater energization is started (see Japanese Unexamined Patent Publication 2003-328821 corresponding to U.S. Pat. No. 6,781,098).

In contrast, the diesel engine features in having a low exhaust gas temperature due to its high thermal efficiency. Therefore, for example, when the engine is stopped after a preceding operational state, where the exhaust temperature is kept low (e.g., the temperature in the exhaust pipe is kept equal to or less than 50° C. in an idling operation), condensed water may be accumulated (left) in the exhaust system because of the continuous state of the low exhaust temperature.

However, a conventional heater controlling apparatus determines timing for the heater energization only based on limited information (e.g., the wall temperature of the exhaust pipe) when a following engine operation begins, without considering an influence due to the condensed water accumulated in the preceding engine operation. In this case, the heater energization is performed in a condition, where the condensed water still exists in the exhaust system. Thus, water drop from the above condensed water may be scattered toward the heated sensing element. As a result, the sensing element may be exposed to the water and may be disadvantageously broken.

Also, it may be proposed that the entire heater energization may be delayed in order to limit breakage of the sensing element due to the exposure to the water. However, unnecessary delay of the heater energization may limit the gas sensor from being quickly activated, and therefore the unnecessary delay may become one cause for limiting purification efficiency of the exhaust gas.

SUMMARY OF THE INVENTION

The present invention is made in view of the above disadvantages. Thus, it is an objective of the present invention to address at least one of the above disadvantages.

To achieve the objective of the present invention, there is provided a heater controlling apparatus for controlling a heater that heats a sensing element of a gas sensor provided in an exhaust system of a diesel engine. The heater controlling apparatus includes a device that changes a reference condition for controlling the heater after a start of the engine in a first operation based on an operational state before a stop of the engine in a second operation, which precedes the first operation.

BRIEF DESCRIPTION OF THE DRAWINGS

The invention, together with additional objectives, features and advantages thereof, will be best understood from the following description, the appended claims and the accompanying drawings in which:

DETAILED DESCRIPTION OF PREFERRED EMBODIMENTS

First Embodiment

A heater controlling apparatus for a gas sensor according to a first embodiment of the present invention will be described with reference to FIGS. 1 to 9.

Figure 1:
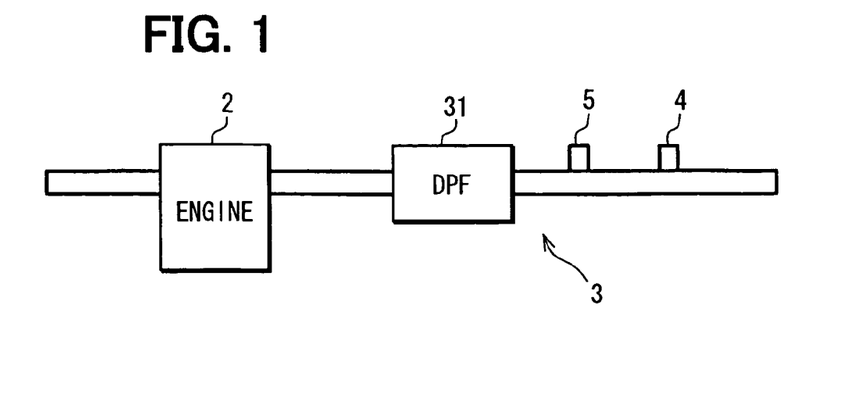
FIG. 1 is an explanatory view of an exhaust system of a diesel engine according to a first embodiment.

A heater controlling apparatus 1 of the present embodiment controls a heater, which heats a sensing element of a gas sensor 4 provided in an exhaust system 3 of a diesel engine 2 as shown in FIG. 1. The heater controlling apparatus 1 is designed to change a reference condition for a heater control after a start of the engine 2 in a following operation (first operation) based on an operational state before a stop of the engine 2 in a preceding operation (second operation), which precedes the following operation (see FIGS. 3 and 4).

In the present embodiment, as shown in FIG. 1, the exhaust system 3 of the diesel engine 2 includes a diesel particulate filter (DPF) 31, an exhaust temperature sensor 5, and a gas sensor 4. Here, the exhaust temperature sensor 5 senses a temperature in the exhaust system 3 downstream of the DPF 31, and the gas sensor 4 senses an oxygen concentration and the like in the exhaust gas.

An air fuel ratio (A/F) sensor, an oxygen sensor, and a nitrogen oxides (NOx) sensor may function as the gas sensor 4. Here, the A/F sensor senses an air fuel ratio of an internal combustion engine based on a limiting current, which depends on the oxygen concentration in the exhaust gas. Also, the oxygen sensor senses the air fuel ratio of the internal combustion engine based on an electromotive force, which depends on the oxygen concentration in the exhaust gas. Also, the NOx sensor senses a concentration of nitrogen oxides (NOx) in the exhaust gas.

A tubular sensing element (not shown) and a layered gas sensing element (not shown) may function as the above sensing element. Here, the tubular sensing element is made of a solid electrolyte, and has a tubular shape with a bottom. The layered gas sensing element is made of a plate solid electrolyte. A ceramic heater (not shown) may function as the above heater. Here, the ceramic heater is provided in contact with the above sensing element or is layered on the above sensing element.

Figure 2:
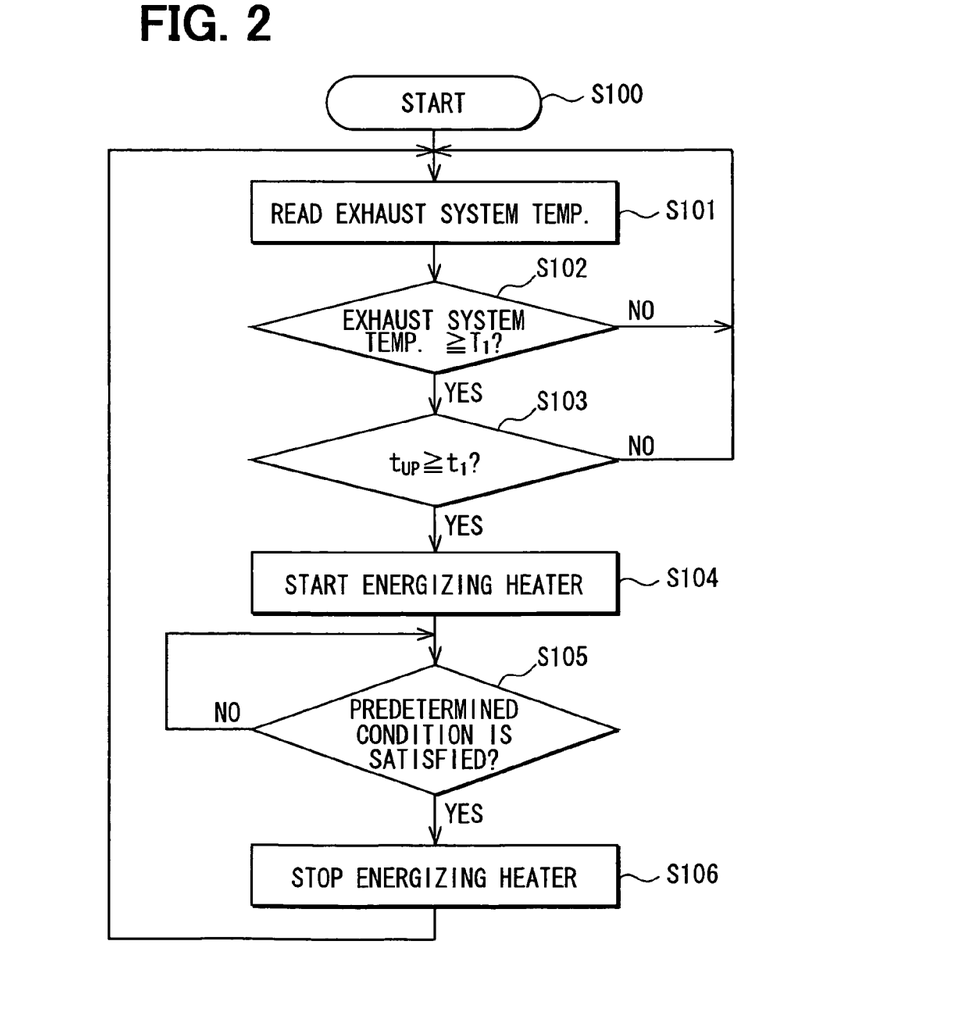
FIG. 2 is an explanatory diagram of a schematic flow of a heater control according to the first embodiment.
Figure 4:
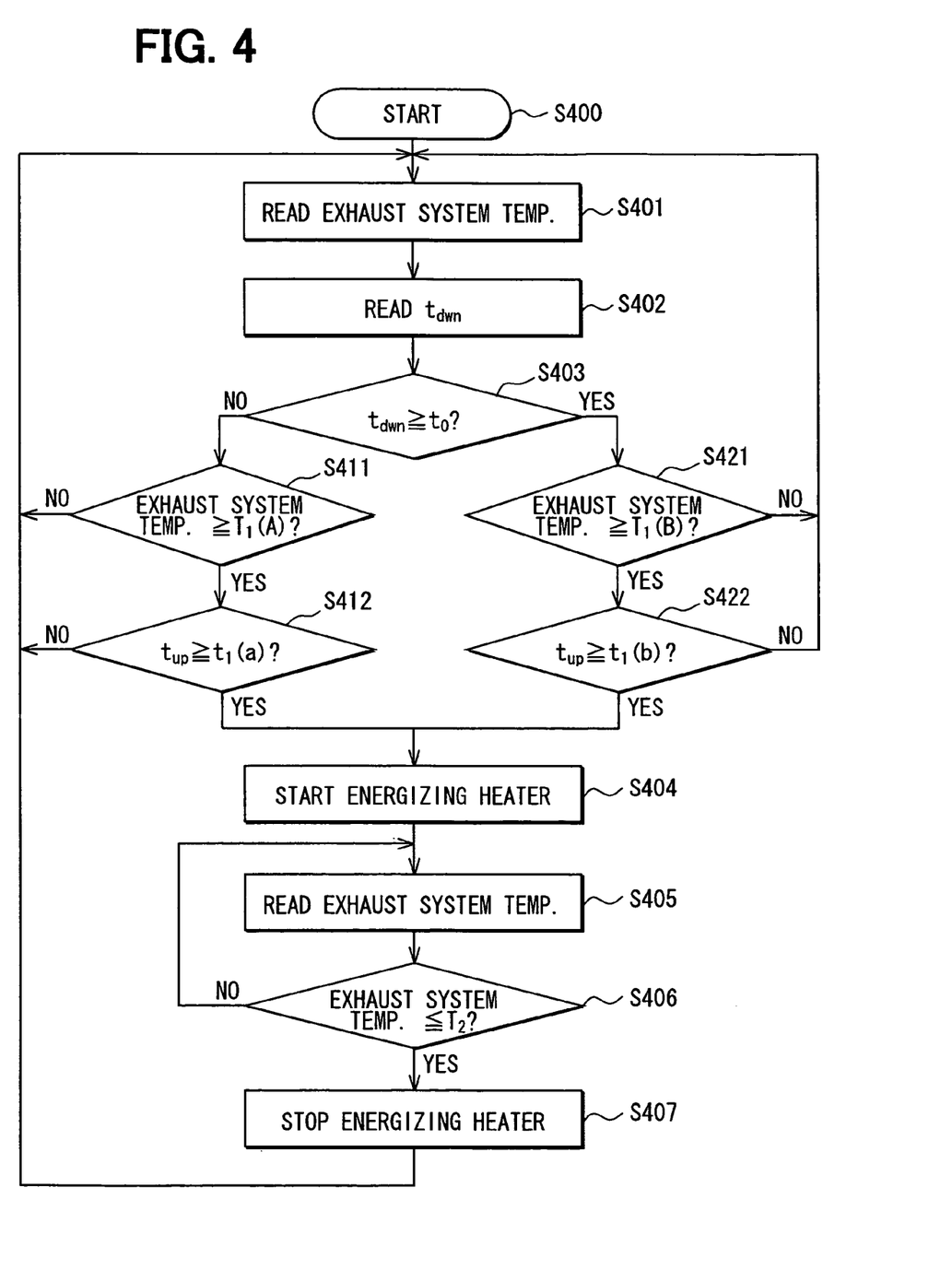
FIG. 4 is an explanatory diagram of a second flow of the heater control after a start of the engine in a following operation according to the first embodiment.
Figure 6:
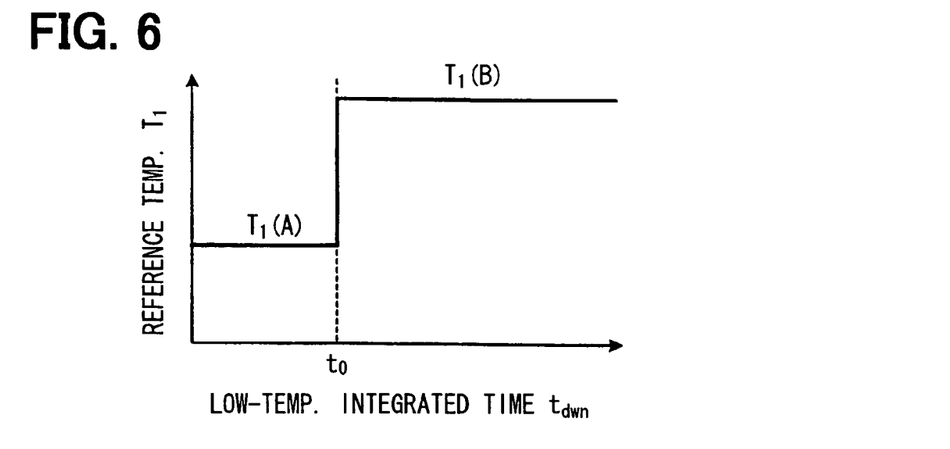
FIG. 6 is a diagram showing a relation between the low-temperature integrated time and a reference temperature according to the first embodiment.
Figure 7:
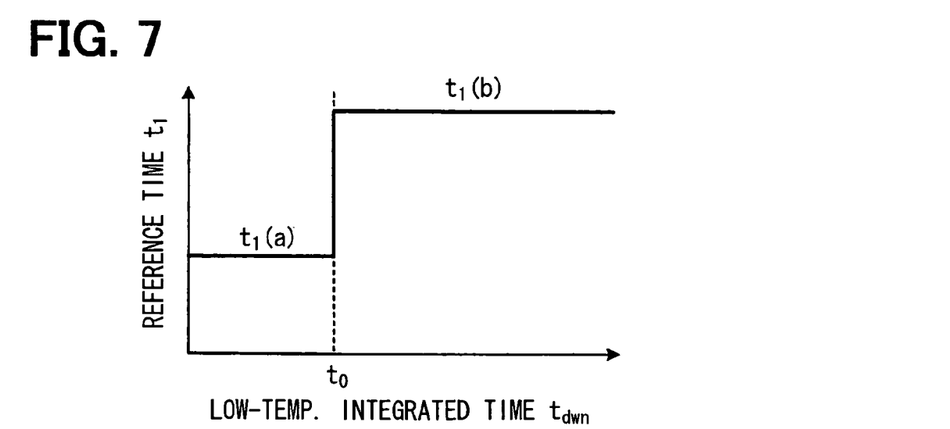
FIG. 7 is a diagram showing a relation between the low-temperature integrated time and a reference time according to the first embodiment.

As shown in FIG. 2, control starts with step S100. Then, the heater controlling apparatus 1 reads the temperature of the exhaust system 3 at step S101, and determines whether the exhaust system temperature is equal to or larger than a predetermined reference temperature $T_1$ at step S102. The heater controlling apparatus 1 is basically designed to start a heater energization (i.e., start energizing the heater) at step S104 when a high-temperature integrated time $t_{up}$ is equal to or larger than a predetermined reference time $t_1$ at step S103. Here, the high-temperature integrated time $t_{up}$ is an integrated time (elapsed time), during which the temperature in the exhaust system 3 is equal to or larger than the predetermined reference temperature $T_1$. When a predetermined condition for stopping the heater energization, which will be described later, is satisfied at step S105, the heater energization is stopped at step S106, and the control returns to step S101. However, as shown in FIGS. 4, 6, and 7, values of the above reference temperature $T_1$ and the reference time $t_1$ are designed to be changed based on the operational state before the engine stop in the preceding operation. In other words, the reference temperature $T_1$ may be set as a reference temperature $T_1(A)$ and a reference temperature $T_1(B)$ based on the operational state before the engine stop in the preceding operation. Also, the reference time $t_1$ may be set as a reference time $t_1(a)$ and $t_1(b)$ based on the above operational state.

That is, the heater controlling apparatus 1 starts energizing the heater when the high-temperature integrated time $t_{up}$ is equal to or larger than a predetermined reference time ($t_1$). Also, the heater controlling apparatus 1 changes each value of at least one of the reference temperature $T_1$ and the reference time $t_1$ based on the operational state before the stop of the engine 2 in the preceding operation (second operation).

Then, the operational state before the engine stop in the preceding operation includes two cases. In one case, a low-temperature integrated time $t_{dwn}$ is equal to or larger than a predetermined reference time (comparative time) $t_0$. In another case, the low-temperature integrated time $t_{dwn}$ is smaller than the predetermined reference time $t_0$. Here, the low-temperature integrated time $t_{dwn}$ is an integrated time, during which the temperature in the exhaust system 3 is equal to or smaller than a predetermined reference temperature (predetermined comparative temperature) $T_0$. In this way, the reference condition of the heater control after the engine start in the following operation is changed correspondingly to the two cases of the preceding operational state.

Thus, the heater controlling apparatus 1 changes the reference condition for controlling the heater after the start of the engine 2 in the following operation (first operation) based on whether the low-temperature integrated time $t_{dwn}$ is equal to or larger than the predetermined comparative time $t_0$ or not.

That is, when the low-temperature integrated time $t_{dwn}$ is smaller than the reference time $t_0$, the reference temperature $T_1$ is set as the reference temperature $T_1(A)$, and also the reference time $t_1$ is set as the reference time $t_1(a)$. When the low-temperature integrated time $t_{dwn}$ is equal to or larger than the reference time $t_0$, the reference temperature $T_1$ is set as the reference temperature $T_1(B)$, and also the reference time $t_1$ is set as the reference time $t_1(b)$. Here, there are following relationships among the above values. $T_1(A)<T_1(B)$, and $t_1(a)<t_1(b)$.

That is, the heater controlling apparatus 1 makes each value of at least one of the reference temperature $T_1$ and the reference time $t_1$ larger when the low-temperature integrated time $t_{dwn}$ is equal to or larger than the comparative time $t_0$, than when the low-temperature integrated time $t_{dwn}$ is smaller than the comparative time $t_0$.

Next, the heater controlling apparatus 1 of the present embodiment will be more specifically described.

Figure 5:
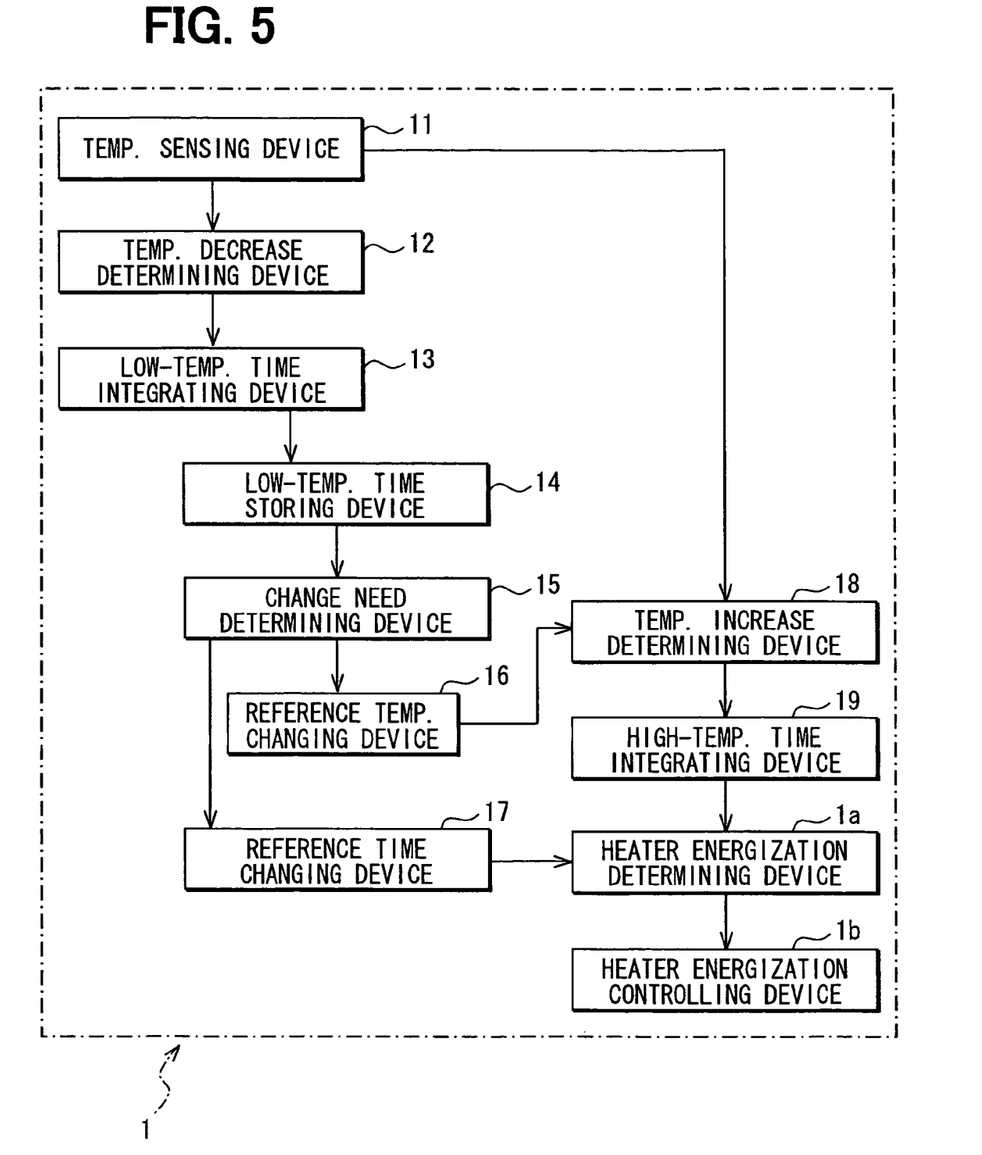
FIG. 5 is a conceptual diagram of a heater controlling apparatus for a gas sensor according to the first embodiment.

As shown in FIG. 5, the heater controlling apparatus 1 includes a temperature sensing device 11, a temperature decrease determining device 12, a low-temperature time integrating device 13, a low-temperature integrated time storing device 14, a reference condition change need determining device 15, a reference temperature changing device (reference condition changing device) 16, a reference time changing device (reference condition changing device) 17, a temperature increase determining device 18, a high-temperature time integrating device 19, a heater energization determining device 1a, and a heater energization controlling device 1b.

The temperature sensing device 11 senses the temperature in the exhaust system 3, and corresponds to the above exhaust temperature sensor 5 shown in FIG. 1.

The temperature decrease determining device 12 determines whether the temperature in the exhaust system 3 is equal to or smaller than the reference temperature $T_0$.

The low-temperature time integrating device 13 measures the low-temperature integrated time $t_{dwn}$.

The low-temperature integrated time storing device 14 stores the low-temperature integrated time $t_{dwn}$.

The reference condition change need determining device 15 determines the need for changing the reference temperature $T_1$ and the reference time $t_1$ based on whether the low-temperature integrated time $t_{dwn}$ is equal to or larger than the reference time (comparative time) $t_0$.

The reference temperature changing device 16 changes the reference temperature $T_1$ based on a determination result of the reference condition change need determining device 15.

The reference time changing device 17 changes the reference time $t_1$ based on the determination result of the reference condition change need determining device 15.

The temperature increase determining device 18 determines whether the temperature in the exhaust system 3 is equal to or larger than the reference temperature $T_1$.

The high-temperature time integrating device 19 measures the high-temperature integrated time $t_{up}$.

The heater energization determining device 1a determines whether it is possible to energize the heater based on whether the high-temperature integrated time $t_{up}$ is equal to or larger than the reference time $t_1$.

The heater energization controlling device 1b energizes the heater based on a determination result of the heater energization determining device 1a.

The heater controlling apparatus 1 performs a below-described control using the above devices based on flows shown in FIGS. 3 and 4.

Figure 3:
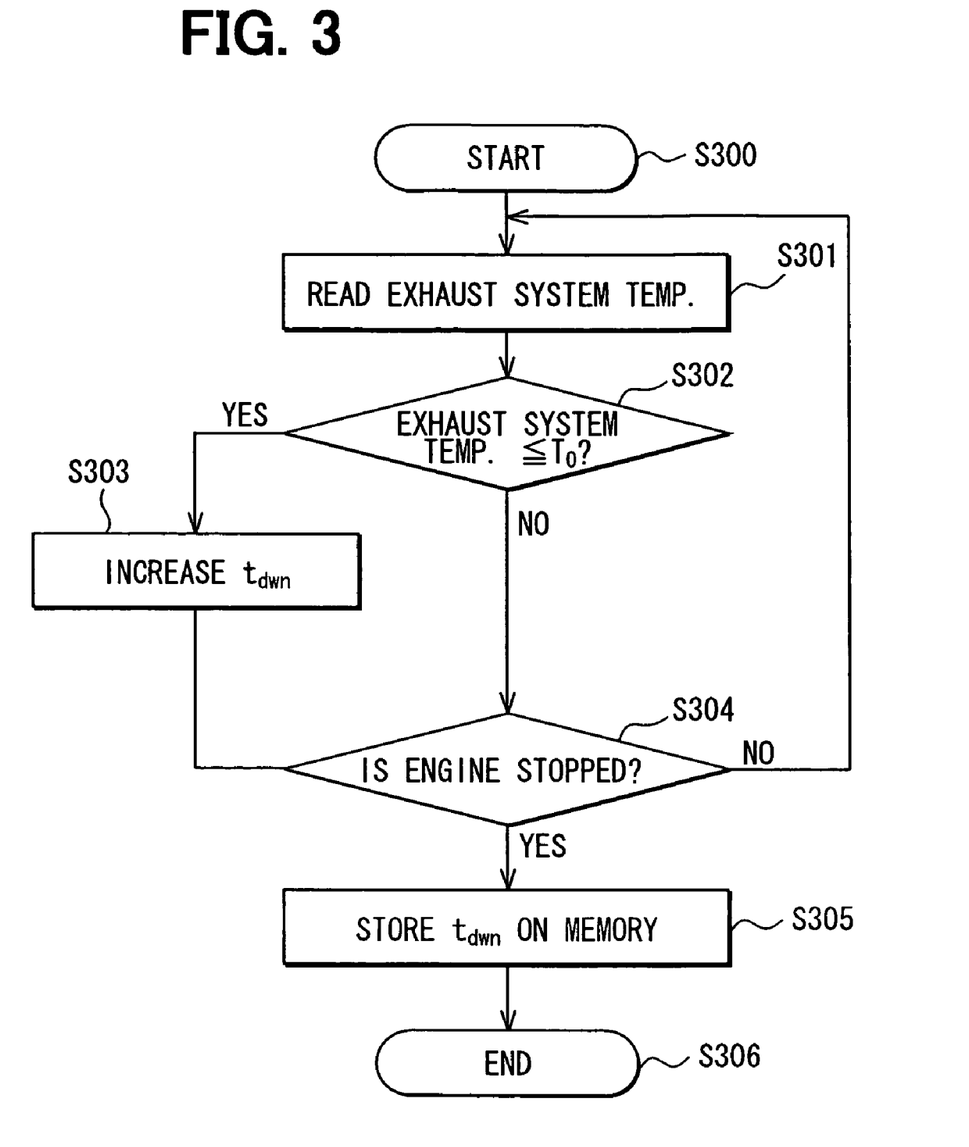
FIG. 3 is an explanatory diagram of a first flow for computing a low-temperature integrated time based on an operational state before a stop of the engine in a preceding operation according to the first embodiment.

FIG. 3 shows a control flow (first flow) for determining the operational state before the engine stop in the preceding operation (second operation). At step S300, control of the first flow is started. The temperature in the exhaust system 3 sensed by the temperature sensing device 11 (exhaust temperature sensor 5) is read at step S301. Next, it is determined at step S302 whether the temperature in the exhaust system 3 (exhaust system temperature) is equal to or smaller than the predetermined reference temperature $T_0$ (comparative temperature) by the temperature decrease determining device 12.

When the temperature decrease determining device 12 determines that the exhaust system temperature is equal to or less than the reference temperature $T_0$, the low-temperature time integrating device 13 increases the low-temperature integrated time $t_{dwn}$ at step S303. Then, the control continues with step S304. When the exhaust system temperature is determined to be larger than the reference temperature $T_0$, the control continues with step S304 without increasing the low-temperature integrated time $t_{dwn}$.

Here, the low-temperature integrated time $t_{dwn}$ is computed during a period from a first timing to a second timing. For example, at the first timing, the heater is temporally deenergized due to the decrease of the exhaust temperature, and also at the second timing, the heater can be energized again. In the above steps, the low-temperature integrated time $t_{dwn}$ may be assumed to be a parameter, which corresponds to an amount of the condensed water in the exhaust pipe.

Next, it is determined whether the engine is stopped (ignition is turned off) or not at step S304. When the engine is stopped, the low-temperature integrated time $t_{dwn}$ is stored on a memory (the low-temperature integrated time storing device 14) at step S305, and then, the first flow is ended at step S306.

In contrast, when the engine is not stopped at step S304, the control returns to step S301 again to read the temperature in the exhaust system 3.

Through the above first flow, the low-temperature integrated time $t_{dwn}$ can be stored as an operational history. Here, the low-temperature integrated time $t_{dwn}$ corresponds to an assumed amount of the condensed water in the exhaust pipe, and the assumed amount changes depending on the operational state before the engine stop.

Next, a second flow will be described with reference to FIG. 4. In the second flow, the low-temperature integrated time $t_{dwn}$ computed in the first flow is used for the heater control after the engine start (turning on of an ignition) in the following operation (first operation), which follows the preceding operation (second operation).

Firstly, a control of the present flow is started at step S400. The temperature in the exhaust system 3 sensed by the temperature sensing device 11 is read at step S401. Next, the low-temperature integrated time $t_{dwn}$ obtained in the first flow is read from the low-temperature integrated time storing device 14 at step S402.

Next, it is determined at step S403 whether the low-temperature integrated time $t_{dwn}$ is equal to or larger than the predetermined reference time (comparative time) $t_0$. That is, the reference condition change need determining device 15 determines the need for changing the reference temperature $T_1$ and the reference time $t_1$.

Here, as shown in FIGS. 6 and 7, when the low-temperature integrated time $t_{dwn}$ is less than the reference time $t_0$ (when it is determined that the reference temperature $T_1$ and the reference time $t_1$ do not need to be changed), the reference temperature $T_1$ is set at $T_1(A)$, and also the reference time $t_1$ is set at $t_1(a)$. In contrast, when the low-temperature integrated time $t_{dwn}$ is equal to or larger than the reference time $t_0$ (when it is determined that the reference temperature $T_1$ and the reference time $t_1$ need to be changed), the reference temperature $T_1$ is set at $T_1(B)$, and also the reference time $t_1$ is set at $t_1(b)$. Here, there is the following relationships. In the reference temperature, $T_1(B)>T_1(A)$, and in the reference time, $t_1(b)>t_1(a)$.

Therefore, when the low-temperature integrated time $t_{dwn}$ is less than the reference time $t_0$ (when it is determined that the reference temperature $T_1$ and the reference time $t_1$ do not need to be changed), the control continues with step S411. At step S411, it is determined whether the exhaust system temperature is equal to or larger than the reference temperature $T_1(A)$ or not by the temperature increase determining device 18. When the exhaust system temperature is equal to or larger than the reference temperature $T_1(A)$, the high-temperature integrated time $t_{up}$ is measured by the high-temperature time integrating device 19. Here, in this case, the high-temperature integrated time $t_{up}$ corresponds to an integrated time (elapsed time), during which the exhaust system temperature is equal to or larger than the reference temperature $T_1(A)$. Then, it is determined at step S412 whether the high-temperature integrated time $t_{up}$ is equal to or larger than the reference time $t_1(a)$. That is, the heater energization determining device 1a determines whether it is appropriate to perform the heater energization or not.

When the high-temperature integrated time $t_{up}$ is equal to or larger than the reference time $t_1(a)$, the heater energization controlling device 1b starts the heater energization control at step S404 for energizing the heater. The energization of the heater in this embodiment corresponds to energization, through which the heater can heat the sensing element to an activation temperature. Even when this energization (i.e., the present energization) is not performed, an auxiliary energization may be usually performed to keep the sensing element at a temperature (e.g., about 100° C. to 200° C.). Here, if not specified, the energization of the present specification does not include this auxiliary energization. Also, the heater energization in this specification does not include a weaker energization of the heater weaker than the above-described present energization.

When each determination at steps S411, S412 is NO (i.e., when the exhaust system temperature is less than the reference temperature $T_1(A)$, or the high-temperature integrated time $t_{up}$ is less than the reference time $t_1(a)$), the control returns to step S401 again to read the exhaust system temperature.

In contrast, when the low-temperature integrated time $t_{dwn}$ is equal to or larger than the reference time (comparative time) $t_0$ (when it is determined that the reference temperature $T_1$ and the reference time $t_1$ need to be changed), the control continues with step S421. At step S421, the temperature increase determining device 18 determines whether the exhaust system temperature is equal to or larger than the reference temperature $T_1(B)$ or not.

When the exhaust system temperature is equal to or larger than the reference temperature $T_1(B)$, the high-temperature integrated time $t_{up}$ is measured by the high-temperature time integrating device 19. Here, in this case, the high-temperature integrated time $t_{up}$ corresponds to an integrated time (elapsed time), during which the exhaust system temperature is equal to or larger than the reference temperature $T_1(B)$. Then, it is determined at step S422 whether the high-temperature integrated time $t_{up}$ is equal to or larger than the reference time $t_1(b)$. That is, the heater energization determining device 1a determines whether it is appropriate to perform the heater energization or not.

When the high-temperature integrated time $t_{up}$ is equal to or larger than the reference time $t_1(b)$, the heater energization controlling device 1b starts the heater energization control at step S404.

When each determination at steps S421, S422 is NO (i.e., when the exhaust system temperature is less than the reference temperature $T_1(B)$, or the high-temperature integrated time $t_{up}$ is less than the reference time $t_1(b)$), the control returns to step S401 again to read the exhaust system temperature.

The followings will describe why it is determined at step S403 whether the low-temperature integrated time $t_{dwn}$ is equal to or larger than the reference time $t_0$ or not.

The reason is that when a value equal to or larger than the reference time $t_0$ is stored as the low-temperature integrated time $t_{dwn}$, it is indicated that the exhaust temperature shifts at lower temperatures before the engine stop (turning of an ignition) in the preceding operation. Thus, it can be assumed that a large amount of the condensed water may be left (accumulated) in the exhaust pipe. Therefore, the reference temperature $T_1$ and the reference time $t_1$ need to be set at larger values compared with those $T_1(A)$, $t_1(a)$ in a case where the low-temperature integrated time $t_{dwn}$ is less than the reference time (comparative time) $t_0$. This is because a larger amount of heat quantity needs to be provided such that the above-condensed water in the exhaust pipe can be effectively evaporated.

Thus, when the low-temperature integrated time $t_{dwn}$ is equal to or larger than the reference time $t_0$, the reference temperature $T_1(B)$ is set as a threshold temperature in the exhaust system, and also the reference time $t_1(b)$ is set as a threshold elapsed time for the reference temperature $T_1(B)$ such that the condensed water left in the exhaust pipe can be completely evaporated. Thus, the heater energization control, in which an influence of the left condensed water before the engine stop in the preceding operation is effectively considered, can be achieved.

Next, when the heater energization is once started at step S404, the exhaust system temperature sensed by the temperature sensing device 11 is again read at step S405. Then, it is determined at step S406 whether the exhaust temperature is equal to or less than another predetermined reference temperature $T_2$ or not. Here, the reference temperature $T_2$ is set independently from the above reference temperature $T_1$, and is less than the reference temperature $T_1$. When the determination at step S406 is NO (i.e., when the exhaust system temperature is larger than the reference temperature $T_2$), the heater energization control is continued. In contrast, when the determination at step S406 is YES (i.e., when the exhaust system temperature is equal to or smaller than the reference temperature $T_2$), the heater energization is stopped (i.e., the heater is deenergized) at step S407. After the heater energization is stopped, the control returns to step S401 again to continue this second flow.

Figure 8:
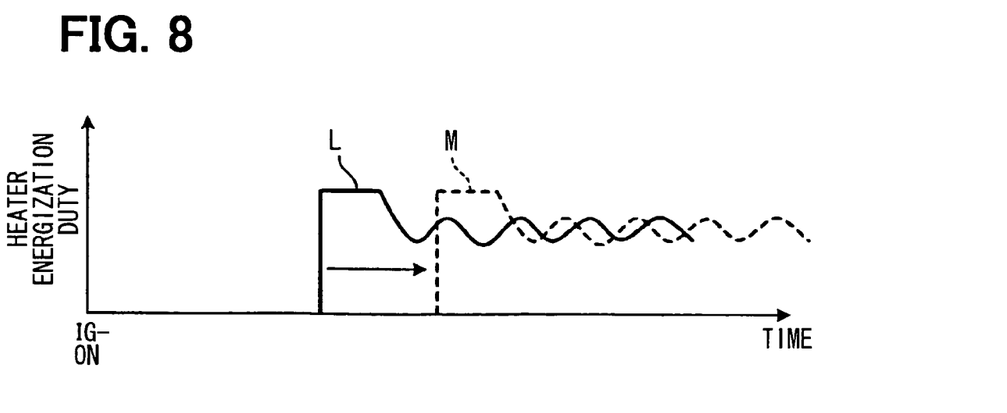
FIG. 8 is a diagram showing a time period for heater energization according to the first embodiment.

When the above first flow and the second flow are operated, the following is achieved. For example, as shown in FIG. 8, when the low-temperature integrated time $t_{dwn}$ is equal to or larger than the reference time $t_0$, a delayed heater energization control (indicated by a dashed line M) is performed. In the delayed heater energization control, start timing of the energization is delayed from that of another heater energization control (indicated by a solid line L) performed when the low-temperature integrated time $t_{dwn}$ is less than the reference time (comparative time) $t_0$.

Next, effects of the present embodiment will be described.

Figure 9:
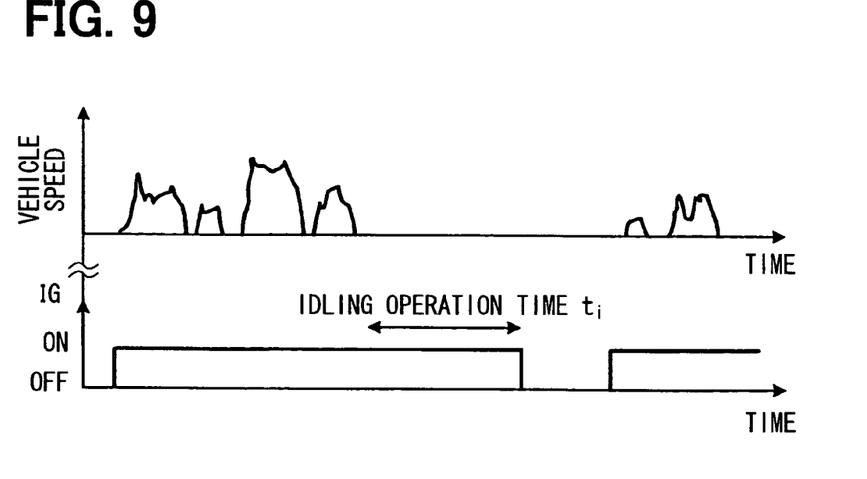
FIG. 9 is a diagram showing time profiles of a vehicle speed and an ignition ON/OFF according to the first embodiment.

The heater controlling apparatus 1 changes the reference condition for the heater control after the engine start in the following operation (first operation) based on the preceding operational state before the engine stop in the preceding operation (second operation). Thus, when there is a certain operational state, where the condensed water is more likely to be left in the exhaust system 3, before the engine stop in the preceding operation, the heater energization after the engine start in the following operation is delayed under consideration of the above certain operational state in the preceding operation. As a result, the sufficient amount of heat quantity can be provided to the exhaust system 3 so that the heater energization can be started after an appropriate remedy, such as the sufficient removal of the condensed water. That is, in a case where an idling operation time $t_i$, during which the vehicle does not move, lasts long in the preceding operation as shown in FIG. 9, the start timing of the heater energization can be delayed as shown in FIG. 8. Here, an upper chart in FIG. 9 shows a time profile of a vehicle speed in a certain vehicle operational pattern. Also, a lower chart in FIG. 9 shows a time profile of an ignition ON/OFF (engine start/stop) correspondingly to the time of the upper chart.

Therefore, even when a large amount of the condensed water is left in the exhaust system 3 during the preceding operation, the heater for the gas sensor can be energized in the following operation in a condition, where the condensed water has been sufficiently removed. Therefore, the sensing element, a temperature of which becomes high, is limited from being exposed to the water. Thus, the breakage of the sensing element can be limited.

Also, when there is not the above certain operational state before the engine stop in the preceding operation (e.g., when the idling operation time $t_i$ shown in FIG. 9 is short), the heater energization after the engine start in the following operation may not be delayed. Typically, in the certain operational state of the present embodiment, the condensed water is more likely to be left in the exhaust system 3. Therefore, the gas sensor can be activated sooner and reliable purification efficiency for the exhaust gas can be achieved.

That is, when the low-temperature integrated time $t_{dwn}$ is smaller than the reference time $t_0$, it may be determined that condensed water is comparatively less likely to be left (accumulated) in the exhaust system 3. In this case, the heater energization may not be delayed.

Because an operational condition for the heater energization can be changed based on the operational requirement, performance of the gas sensor 4 can be sufficiently realized and also the sensing element can be effectively limited from being broken due to the exposure to the water.

Also, the above heater controlling apparatus 1 is structured to change the reference temperature $T_1$ and the reference time $t_1$ based on the operational state before the engine stop in the preceding operation. That is, the reference temperature $T_1$ can be set at $T_1(A)$ and $T_1(B)$ based on the preceding operational state. Also, the reference time $t_1$ can be set at $t_1(a)$ and $t_1(b)$ based on the preceding operational state.

Therefore, when the condensed water is likely to be left in the exhaust system 3 in the operational state before the engine stop in the preceding operation, the sensing element can be heated after the condensed water is sufficiently removed by elongating the reference temperature $T_1$ and the reference time $t_1$. As a result, the sensing element can be effectively limited from being broken due to the exposure to the water.

The reference condition for the heater control after the engine start in the following operation is changed based on whether the low-temperature integrated time $t_{dwn}$ is equal to or larger than the predetermined reference time $t_0$ or not.

Therefore, the reference condition for the heater control after the engine start in the following operation is changed based on whether or not the preceding operation is performed under an operational state, where the condensed water is likely to be left in the exhaust system 3 before the engine stop.

As a result, the performance of the gas sensor 4 can be sufficiently realized, and also the sensing element can be effectively limited from being broken due to the exposure to the water.

In other words, in the present embodiment, values for the reference temperature $T_1$ and the reference time $t_1$ are set larger when the low-temperature integrated time $t_{dwn}$ is equal to or larger than the predetermined reference time (comparative time) $t_0$, compared with those when the low-temperature integrated time $t_{dwn}$ is less than the predetermined reference time $t_0$. Therefore, it can be determined whether the reference temperature $T_1$ and the reference time $t_1$ for the heater control after the engine start in the following operation are to be increased or not based on whether or not the preceding operation is performed under the operational state, where the condensed water is likely to be left in the exhaust system 3 before the engine stop. As a result, the performance of the gas sensor 4 can be sufficiently realized, and also the sensing element can be effectively limited from being broken due to the exposure to the water.

As above, the prevent embodiment can provide a heater controlling apparatus for a gas sensor, which can effectively limit the sensing element from being broken due to the exposure to the water.

Second Embodiment

Figure 10:
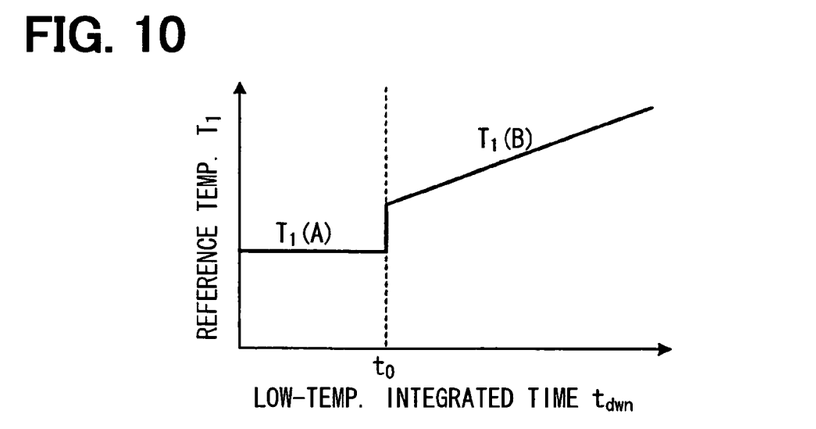
FIG. 10 is a diagram showing a relation between the low-temperature integrated time and the reference temperature according to a second embodiment.
Figure 11:
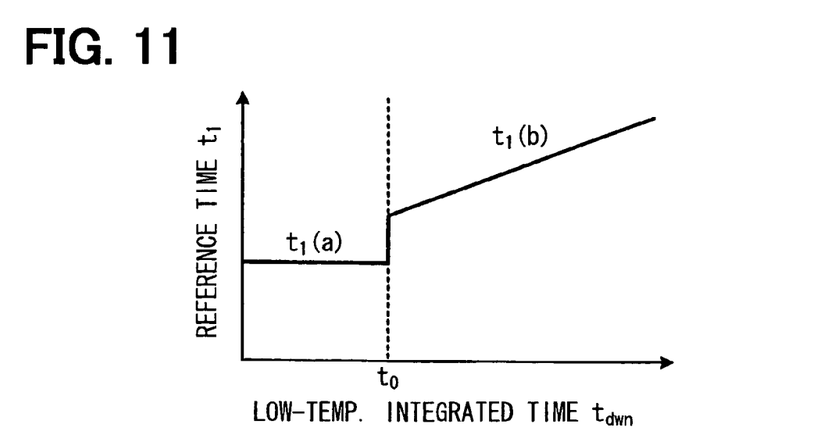
FIG. 11 is a diagram showing a relation between the low-temperature integrated time and the reference time according to the second embodiment.

A heater controlling apparatus for a gas sensor of the second embodiment of the present invention will be described with reference to FIGS. 10 and 11. Similar components and reference condition of the heater controlling apparatus of the present embodiment, which are similar to the components and the condition of the heater controlling apparatus of the first embodiment, will be indicated by the same numerals. In this embodiment, a magnitude of each value of the reference temperature $T_1(B)$ and the reference time $t_1(b)$ are changed in proportion to a magnitude of the low-temperature integrated time $t_{dwn}$. That is, the heater controlling apparatus 1 increases each value of the at least one of the predetermined reference temperature $T_1$ and the predetermined reference time $t_1$ in proportion to the magnitude of the low-temperature integrated time $t_{dwn}$.

In the present embodiment, the reference temperature $T_1(B)$ and the reference time $t_1(b)$, which are used when the low-temperature integrated time $t_{dwn}$ is equal to or larger than the reference time $t_0$, are not constant differently from those described in the first embodiment. The reference temperature $T_1(B)$ and the reference time $t_1(b)$ are set larger as the low-temperature integrated time $t_{dwn}$ becomes larger as shown in FIGS. 10 and 11.

Other aspects of the second embodiment are similar to the first embodiment.

In the present embodiment, the performance of the gas sensor 4 can be more sufficiently realized, and also the sensing element can be more effectively limited from being broken due to the exposure to the water. That is, even when the low-temperature integrated time $t_{dwn}$ exceeds the reference time $t_0$, the left condensed water may be assumed to be small if the exceeding amount of the low-temperature integrated time $t_{dwn}$ over the reference time $t_0$ is small. Thus, in this case, an increase amount of each of the reference temperature $T_1$ and the reference time $t_1$ may be set smaller.

Also, when the low-temperature integrated time $t_{dwn}$ exceeds the reference time $t_0$ by a large amount, the left condensed water may be assumed to be larger. Thus, in this case, the increase amount of each of the reference temperature $T_1$ and the reference time $t_1$ may be set larger.

Therefore, the start timing of the heater energization can be delayed as needed. As a result, the gas sensor 4 can be activated sooner, and also the sensing element can be effectively limited from being broken due to the exposure to the water.

Also, in the second embodiment, similar effects similar to those of the first embodiment can be achieved.

Third Embodiment

Figure 12:
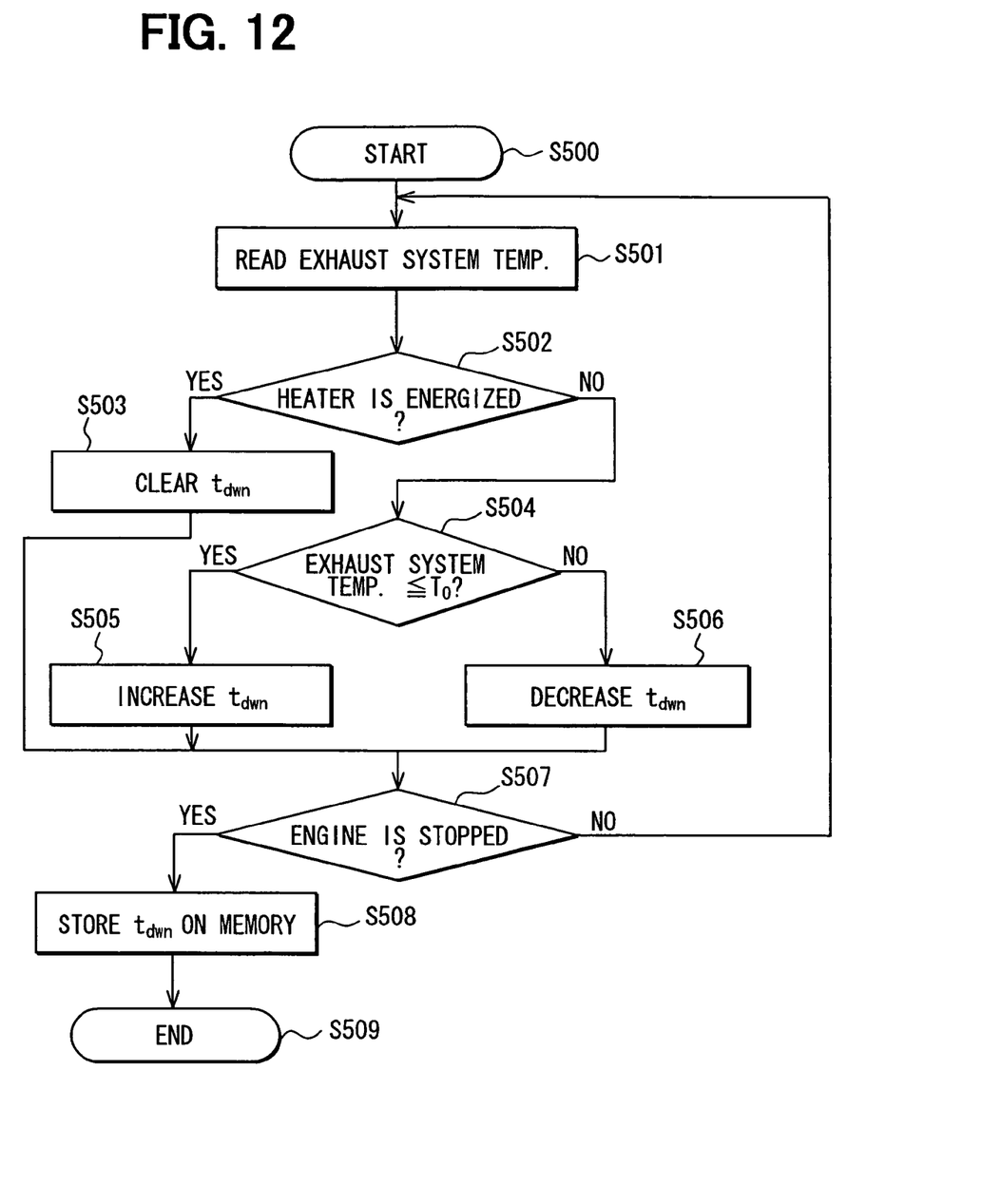
FIG. 12 is an explanatory diagram of a first flow for computing a low-temperature integrated time based on the operational state before the stop of the engine in the preceding operation according to a third embodiment.

The third embodiment of the present invention will be described with reference to FIG. 12. Similar components and reference condition of the heater controlling apparatus of the present embodiment, which are similar to the components and the condition of the heater controlling apparatus of the first embodiment, will be indicated by the same numerals. FIG. 12 shows another first flow of a heater controlling apparatus for a gas sensor, in which the first flow in the first embodiment for determining the operational state before the engine stop in the preceding operation is changed.

In other words, similar to the first embodiment, the first flow control is started at step S500, and the temperature in the exhaust system 3 is read by the temperature sensing device 11 at step S501.

Then, it is determined whether the heater is energized or not at step S502.

Then, when the heater is energized, the low-temperature integrated time $t_{dwn}$ is cleared (in one embodiment, the integrated time $t_{dwn}$ is set zero) at step S503. Then, the control continues with step S507. In contrast, when the heater is not energized, it is determined at step S504 whether the exhaust system temperature is equal to or less than the predetermined temperature $T_0$ by the temperature decrease determining device 12.

The objective of the first flow of the present embodiment is to more effectively store an integrated time (elapsed time) of a certain condition (e.g., an idling operation), where the exhaust temperature decreases, before the engine stop. Therefore, when the heater is energized, the low-temperature integrated time $t_{dwn}$ is cleared because in this case, it is determined (assumed) that there is no water in the exhaust pipe.

When the temperature decrease determining device 12 determines that the exhaust system temperature is equal to or less than the reference temperature $T_0$ at step S504, the low-temperature integrated time $t_{dwn}$ is increased at step S505. When the temperature decrease determining device 12 determines that the exhaust system temperature is larger than the reference temperature $T_0$ at step S504, the low-temperature integrated time $t_{dwn}$ is increased at step S506. Here, when the low-temperature integrated time $t_{dwn}$ becomes zero, the low-temperature integrated time $t_{dwn}$ is not decreased further.

Here, an exhaust temperature decrease time is computed during an integrated time (elapsed time) from the first timing to the second timing. Here, for example, at the first timing, the heater is temporally deenergized due to the decrease of the exhaust temperature, and also at the second timing, the heater can be energized again. The exhaust temperature decrease time is assumed to correspond to the amount of the condensed water in the exhaust pipe. When the exhaust system temperature exceeds the reference temperature (comparative temperature) $T_0$, the low-temperature integrated time $t_{dwn}$ is decreased because the condensed water in the exhaust pipe may be assumed to be evaporated and decreased.

Next, it is determined whether the engine 2 is stopped (ignition is turned off) or not at step S507. When the engine is stopped, the low-temperature integrated time $t_{dwn}$ is stored on the memory (the low-temperature integrated time storing device 14) at step S508, and the first flow is ended at step S509.

In contrast, when it is determined that the engine is not stopped at step S507, the control returns to step S501 again to read the temperature in the exhaust system 3.

Through the above first flow, the low-temperature integrated time $t_{dwn}$ can be stored as an operational history. Here, the low-temperature integrated time $t_{dwn}$ corresponds to the assumed amount of the condensed water in the exhaust pipe, and the assumed amount changes depending on the operational state before the engine stop. Then, the low-temperature integrated time $t_{dwn}$ is reflected on the heater control for the gas sensor 4 after the engine start in the following operation (first operation).

Other aspects of the second embodiment are similar to the first embodiment.

In the present embodiment, the heater control can be performed more accurately corresponding to the assumed amount of the condensed water in the exhaust system 3. Therefore, in the heater control of the present embodiment, the element can be more effectively limited from being broken.

In the third embodiment, similar effects similar to those of the first embodiment can be also achieved.

Comparative Example

Figure 13:
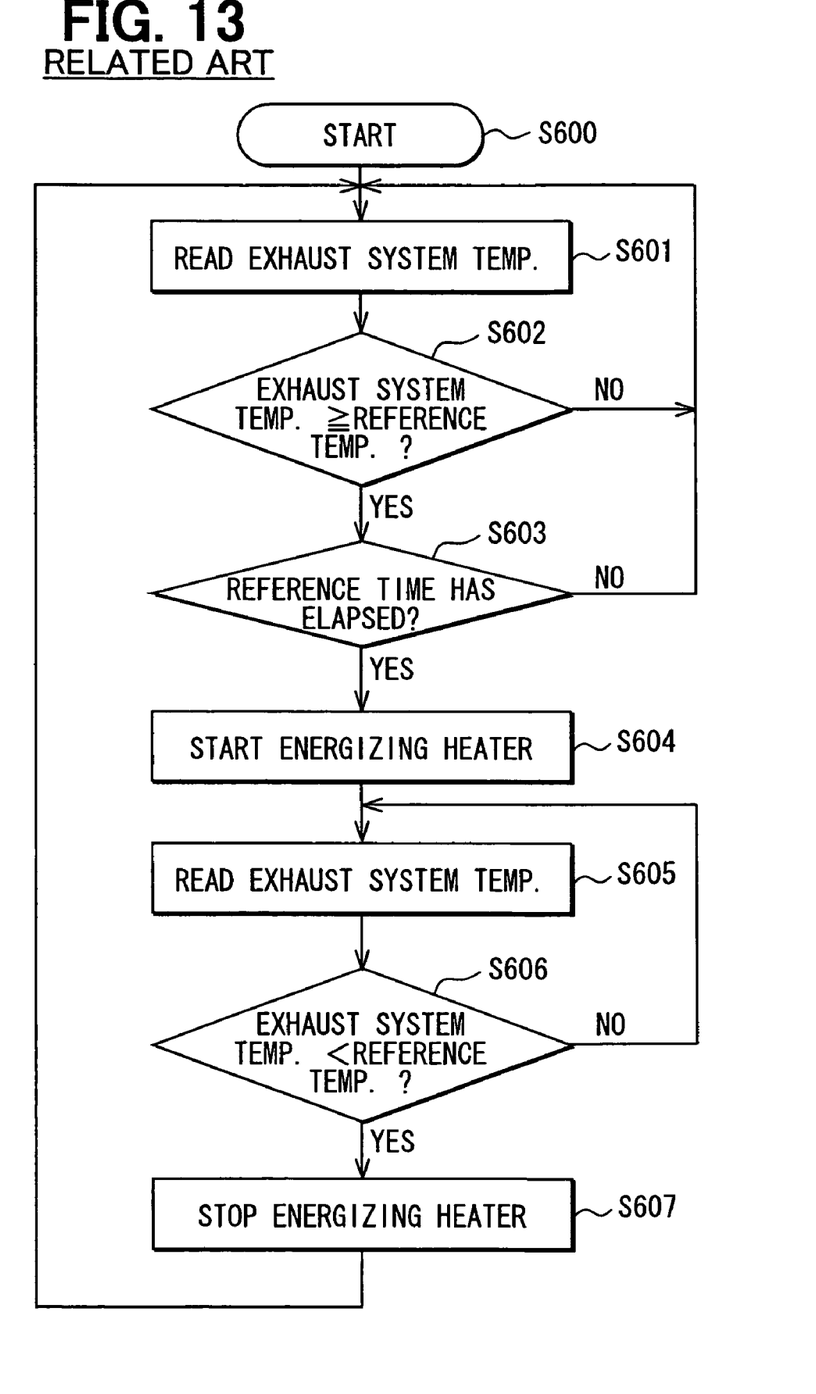
FIG. 13 is an explanatory diagram of a flow for a heater control according to a comparative example.

The present comparative example, which is different from the above embodiments of the present invention, will be described with reference to FIG. 13. In this comparative example, a heater control of a gas sensor after a start of an engine in the following operation is performed without considering an operational state before a stop of the engine in a preceding operation.

Firstly, at step S600, a process of the present flow is started. A temperature in an exhaust system is read at step S601, and it is determined at step S602 whether the temperature is equal to or larger than a predetermined reference temperature.

When a determination at step S602 is NO (i.e., the exhaust system temperature is less than the reference temperature), a present operational state is maintained. When the determination at step S602 is YES (i.e., the exhaust system temperature is equal to or larger than the reference temperature), the control continues with step S603. At step S603, it is determined whether a predetermined reference time has elapsed or not. When the determination at step S603 is YES, it is determined that water is removed in the exhaust system. Then, heater energization is started at step S604.

Even after the heater energization is started, the temperature in the exhaust system is read at step S605. Then, at step S606, it is determined whether the exhaust system temperature is less than a predetermined reference temperature or not. When a determination at step S606 is NO (when the exhaust system temperature is equal to or larger than the reference temperature), the heater energization is continued. When the determination is YES (when the exhaust system temperature is less than the reference temperature), the heater energization is stopped at step S607. Then, the control returns to step S601, and the control waits for an increase of the temperature at steps S601 to S603.

As described above, in the comparative example, it is determined whether the heater energization can be performed based on whether or not the exhaust system temperature reaches the predetermined temperature, and also based on whether or not the predetermined reference time has elapsed.

However, there may be a case where a large amount of condensed water is left in the exhaust pipe when the exhaust temperature is kept at low for long in, for example, an idling operation before the engine stop in the preceding operation.

In this case, even when it is determined at steps S602 and S603 that the exhaust system temperature exceeds the reference temperature and the reference time has elapsed, the water left in the exhaust pipe at the time of stopping the engine in the preceding operation is not considered. Thus, a sufficient degree of accuracy for determining that there is no water left in the exhaust pipe may not be disadvantageously attained if the determination is based only on information of the exhaust system temperature.

In contrast to the comparative example, the heater controlling apparatus of the present invention can highly accurately determine that there is no water left in the exhaust pipe. This is because in the embodiments of the present invention, firstly, the operational state before the engine stop in the preceding operation is stored. Then, the reference condition for the heater control after the engine start in the following operation can be changed based on the stored operational state.

Additional advantages and modifications will readily occur to those skilled in the art. The invention in its broader terms is therefore not limited to the specific details, representative apparatus, and illustrative examples shown and described.

What is claimed is:

1. A heater controlling apparatus for controlling an electric heater that heats a sensing element of a gas sensor provided in an exhaust system of a diesel engine, the heater controlling apparatus comprising:
  information obtaining means for obtaining information used for obtaining an operational state of the exhaust system of the engine; and
  reference condition changing means for changing a reference condition of the electric heater in a current engine operation based on the operational state in a previous engine operation obtained before turning off of the engine in the previous engine operation;
  wherein the information obtaining means is temperature sensing means for sensing a temperature in the exhaust system of the engine, which temperature serves as the information used for obtaining the operational state of the exhaust system of the engine, the heater controlling apparatus further comprising:
  temperature increase determining means for determining whether the temperature in the exhaust system is equal to or larger than a predetermined reference temperature;

high-temperature time integrating means for measuring a high-temperature integrated time in the current engine operation, the high-temperature integrated time being an integrated time, during which the temperature increase determining means determines that the temperature in the exhaust system is equal to or larger than the predetermined reference temperature;

heater energization determining means for determining whether the high-temperature integrated time measured in the current engine operation is equal to or larger than a predetermined reference time; and heater energization controlling means for starting energization of the electric heater when the heater energization determining means determines that the high-temperature integrated time is equal to or larger than the predetermined reference time; and wherein the reference condition changing means changes at least one of the predetermined reference temperature and the predetermined reference time based on the operational state in the previous engine operation.

2. A heater controlling apparatus for controlling an electric heater that heats a sensing element of a gas sensor provided in an exhaust system of a diesel engine, the heater controlling apparatus comprising:

information obtaining means for obtaining information used for obtaining an operational state of the exhaust system of the engine; and reference condition changing means for changing a reference condition of the electric heater in a current engine operation based on the operational state in a previous engine operation obtained before turning off of the engine in the previous engine operation;

wherein the information obtaining means is temperature sensing means for sensing a temperature in the exhaust system of the engine, which temperature serves as the information used for obtaining the operational state of the exhaust system of the engine, the heater controlling apparatus further comprising:

temperature decrease determining means for determining whether the temperature in the exhaust system is equal to or smaller than a predetermined comparative temperature;

low-temperature time integrating means for measuring a low-temperature integrated time before turning off of the engine in the previous engine operation, the low-temperature integrated time being an integrated time, during which the temperature decrease determining means determines that the temperature in the exhaust system is equal to or smaller than the predetermined comparative temperature; and reference condition change need determining means for determining whether the low-temperature integrated time measured in the previous engine operation is equal to or larger than a predetermined comparative time, a determination result of the reference condition change need determining means serving as the operational state in the previous engine operation; and wherein the reference condition changing means changes the reference condition of the electric heater in the current engine operation based on the determining result of the reference condition change need determining means.

3. The heater controlling apparatus according to claim 2, further comprising:

temperature increase determining means for determining whether the temperature in the exhaust system is equal to or larger than a predetermined reference temperature;

high-temperature time integrating means for measuring a high-temperature integrated time in the current engine operation, the high-temperature integrated time being an integrated time, during which the temperature increase determining means determines that the temperature in the exhaust system is equal to or larger than the predetermined reference temperature;

heater energization determining means for determining whether the high-temperature integrated time measured in the current engine operation is equal to or larger than a predetermined reference time; and heater energization controlling means for starting energization of the electric heater when the heat energization determining means determines that the high-temperature integrated time is equal to or larger than the predetermined reference time; and wherein the reference condition changing means makes a value of at least one of the predetermined reference temperature and the predetermined reference time greater in a first condition than in a second condition:

in the first condition, the reference condition change need determining means determines that the low-temperature integrated time in the previous engine operation is equal to or larger than the predetermined comparative time; and in the second condition, the reference condition change need determining means determines that the low-temperature integrated time in the previous engine operation is smaller than the predetermined comparative time.

4. The heater controlling apparatus according to claim 3, wherein:

the reference condition changing means increases the value of the at least one of the predetermined reference temperature and the predetermined reference time in accordance with the low-temperature integrated time.

5. The heater controlling apparatus according to claim 2, further comprising:

low-temperature time storing means for storing the low-temperature integrated time, wherein the reference condition change need determining means determines whether the low-temperature integrated time stored in the low-temperature time storing means is equal to or larger than the predetermined comparative time.

6. A heater controlling apparatus for controlling an electric heater that heats a sensing element of a gas sensor provided in an exhaust system of a diesel engine, the heater controlling apparatus comprising:

temperature information obtaining means for obtaining temperature information that indicates a temperature of exhaust gas in the exhaust system;

power supply control means for controlling energization of the electric heater, where the power supply control means sets start timing of the energization of the electric heater in a current engine operation based on the temperature information of a previous engine operation obtained before turning off of the engine in the previous engine operation;

temperature increase determining means for determining whether the temperature in the exhaust system is equal to or larger than a predetermined reference temperature;

high-temperature time integrating means for measuring a high-temperature integrated time in the current engine operation, the high-temperature integrated time being an integrated time, during which the temperature increase determining means determines that the temperature in the exhaust system is equal to or larger than the predetermined reference temperature;
heater energization determining means for determining whether the high-temperature integrated time measured in the current engine operation is equal to or larger than a predetermined reference time that corresponds to the start timing of the energization; and
heater energization controlling means for starting energization of the electric heater when the heater energization determining means determines that the high-temperature integrated time is equal to or larger than the predetermined reference time,
wherein the power supply control means changes the predetermined reference time based on the temperature information of the previous engine operation.

7. A heater controlling apparatus for controlling an electric heater that heats a sensing element of a gas sensor provided in an exhaust system of a diesel engine, the heater controlling apparatus comprising:
temperature information obtaining means for obtaining temperature information that indicates a temperature of exhaust gas in the exhaust system; and
power supply control means for controlling energization of the electric heater, where the power supply control means sets start timing of the energization of the electric heater in a current engine operation based on the temperature information of a previous engine operation obtained before turning off of the engine in the previous engine operation, wherein the power supply control means includes:
temperature decrease determining means for determining whether the temperature in the exhaust system is equal to or smaller than a predetermined comparative temperature;
low-temperature time integrating means for measuring a low-temperature integrated time before turning off of the engine in the previous engine operation, the low-temperature integrated time being an integrated time, during which the temperature decrease determining means determines that the temperature in the exhaust system is equal to or smaller than the predetermined comparative temperature;
reference condition change need determining means for determining whether the low-temperature integrated time measured in the previous engine operation is equal to or larger than a predetermined comparative time, a determination result of the reference condition change need determining means corresponding to the temperature information of the previous engine operation; and
reference time changing means for setting the start timing of the electric heater in the current engine operation based on the determination result of the reference condition change need determining means.

8. The heater controlling apparatus according to claim 7, further comprising:
temperature increase determining means for determining whether the temperature in the exhaust system is equal to or larger than a predetermined reference temperature;
high-temperature time integrating means for measuring a high-temperature integrated time in the current engine operation, the high-temperature integrated time being an integrated time, during which the temperature increase determining means determines that the temperature in the exhaust system is equal to or larger than the predetermined reference temperature;
heater energization determining means for determining whether the high-temperature integrated time measured in the current engine operation is equal to or larger than a predetermined reference time that corresponds to the start timing of the energization; and
heater energization controlling means for starting energization of the electric heater when the heater energization determining means determines that the high-temperature integrated time is equal to or larger than the predetermined reference time;
wherein the reference time changing means makes a value of the predetermined reference time greater in a first condition than in a second condition:
in the first condition, the reference condition change need determining means determines that the low-temperature integrated time in the previous engine operation is equal to or larger than the predetermined comparative time; and
in the second condition, the reference condition change need determining means determines that the low-temperature integrated time in the previous engine operation is smaller than the predetermined comparative time.

9. The heater controlling apparatus according to claim 8, wherein the reference time changing means increases the predetermined reference time in accordance with the low-temperature integrated time.

10. The heater controlling apparatus according to claim 7, the power supply control means includes low-temperature time storing means for storing the low-temperature integrated time, wherein the reference condition change need determining means determines whether the low-temperature integrated time stored in the low-temperature time storing means is equal to or larger than the predetermined comparative time.

11. The heater controlling apparatus according to claim 6, the power supply control means includes reference temperature changing means for changing the predetermined reference temperature based on the temperature information of the previous engine operation.

12. A heater controlling apparatus comprising:
an electric heater that heats a sensing element of a gas sensor provided in an exhaust system of a diesel engine;
a temperature sensor that measures a temperature of exhaust gas in the exhaust system; and
a controller that controls energization of the electric heater, wherein the controller sets start timing of the energization of the electric heater in a current engine operation based on the temperature of the exhaust gas measured with the temperature sensor in a previous engine operation before turning off of the engine in the previous engine operation, wherein the controller includes:
temperature increase determining means for determining whether the temperature in the exhaust system is equal to or larger than a predetermined reference temperature;
high-temperature time integrating means for measuring a high-temperature integrated time in the current engine operation, the high-temperature integrated time being an integrated time, during which the temperature increase determining means determines that the temperature in the exhaust system is equal to or larger than the predetermined reference temperature;
heater energization determining means for determining whether the high-temperature integrated time measured in the current engine operation is equal to or larger than a predetermined reference time that corresponds to the start timing of the energization; and
heater energization controlling means for starting energization of the electric heater when the heater energization determining means determines that the high-temperature integrated time is equal to or larger than the predetermined reference time; and the controller changes the predetermined reference time based on the temperature information of the previous engine operation.

13. The heater controlling apparatus according to claim 12, where the controller includes reference temperature changing means for changing the predetermined reference temperature based on the temperature information of the previous engine operation.

14. A heater controlling apparatus comprising:
an electric heater that heats a sensing element of a gas sensor provided in an exhaust system of a diesel engine;
a temperature sensor that measures a temperature of exhaust gas in the exhaust system; and
a controller that controls energization of the electric heater, wherein the controller sets start timing of the energization of the electric heater in a current engine operation based on the temperature of the exhaust gas measured with the temperature sensor in a previous engine operation before turning off of the engine in the previous engine operation, wherein the controller includes:
temperature decrease determining means for determining whether the temperature in the exhaust system is equal to or smaller than a predetermined comparative temperature;
low-temperature time integrating means for measuring a low-temperature integrated time before turning off of the engine in the previous engine operation, the low-temperature integrated time being an integrated time, during which the temperature decrease determining means determines that the temperature in the exhaust system is equal to or smaller than the predetermined comparative temperature;
reference condition change need determining means for determining whether the low-temperature integrated time measured in the previous engine operation is equal to or larger than a predetermined comparative time, a determination result of the reference condition change need determining means corresponding to the temperature information of the previous engine operation; and
reference time changing means for setting the start timing of the electric heater in the current engine operation based on the determination result of the reference condition change need determining means.

15. The heater controlling apparatus according to claim 14, wherein the controller includes:
temperature increase determining means for determining whether the temperature in the exhaust system is equal to or larger than a predetermined reference temperature;
high-temperature time integrating means for measuring a high-temperature integrated time in the current engine operation, the high-temperature integrated time being an integrated time, during which the temperature increase determining means determines that the temperature in the exhaust system is equal to or larger than the predetermined reference temperature;
heater energization determining means for determining whether the high-temperature integrated time measured in the current engine operation is equal to or larger than a predetermined reference time that corresponds to the start timing of the energization; and
heater energization controlling means for starting energization of the electric heater when the heater energization determining means determines that the high-temperature integrated time is equal to or larger than the predetermined reference time;

wherein the reference timing changing means makes a value of the predetermined reference time greater in a first condition than in a second condition:
in the first condition, the reference condition change need determining means determines that the low-temperature integrated time in the previous engine operation is equal to or larger than the predetermined comparative time; and
in the second condition, the reference condition change need determining means determines that the low-temperature integrated time in the previous engine operation is smaller than the predetermined comparative time.

16. The heater controlling apparatus according to claim 15, wherein the reference time changing means increases the predetermined reference time in accordance with the low-temperature integrated time.

17. The heater controlling apparatus according to claim 14, wherein the controller includes:
low-temperature time storing means for storing the low-temperature integrated time, wherein the reference condition change need determining means determines whether the low-temperature integrated time stored in the low-temperature time storing means is equal to or larger than the predetermined comparative time.

18. A heater controlling method for controlling an electric heater that heats a sensing element of a gas sensor provided in an exhaust system of a diesel engine, the heater controlling method comprising:
obtaining temperature information that indicates a temperature of exhaust gas in the exhaust system;
setting start timing of energization of the electric heater in a current engine operation based on the temperature information of a previous engine operation obtained before turning off the engine in the previous engine operation; and
energizing the electric heater at the stall timing in the current engine operation;
wherein the setting of the start timing includes:
determining whether the temperature in the exhaust system in the previous engine operation is equal to or smaller than a predetermined comparative temperature;
measuring a low-temperature integrated time before turning off of the engine in the previous engine operation, the low-temperature integrated time being an integrated time, during which it is determined that the temperature in the exhaust system is equal to or smaller than the predetermined comparative temperature;
determining whether the low-temperature integrated time measured in the previous engine operation is equal to or larger than a predetermined comparative time;
setting the start timing of energization of the electric heater in the current engine operation based on a determination result of the determining of whether the low-temperature integrated time measured in the previous engine operation is equal to or larger than the predetermined comparative time.

19. A heater controlling method for controlling an electric heater that heats a sensing element of a gas sensor provided in an exhaust system of a diesel engine, the heater controlling method comprising:
obtaining temperature information that indicates a temperature of exhaust gas in the exhaust system;
setting start timing of energization of the electric heater in a current engine operation based on the temperature information of a previous engine operation obtained before turning off the engine in the previous engine operation; and energizing the electric heater at the start timing in the current engine operation, wherein the energizing of the electric heater includes:

determining whether the temperature in the exhaust system in the current engine operation is equal to or larger than a predetermined reference temperature;

measuring a high-temperature integrated time in the current engine operation, the high-temperature integrated time being an integrated time, during which the temperature increase determining means determines that the temperature in the exhaust system is equal to or larger than the predetermined reference temperature;

determining whether the high-temperature integrated time measured in the current engine operation is equal to or larger than a predetermined reference time that corresponds to the start timing of the energization; and starting the energization of the electric heater when it is determined that the high-temperature integrated time is equal to or larger than the predetermined reference time.

20. The heater controlling method according to claim 19, wherein:

the setting of the start timing includes changing the predetermined reference time in the current engine operation based on the temperature information of the previous engine operation.

21. The heater controlling method according to claim 19, further comprising:

changing the predetermined reference temperature in the current engine operation based on the temperature information of the previous engine operation.

22. The heater controlling method according to claim 19, wherein:

the setting of the start timing includes storing the low-temperature integrated time in a memory; and the determining of whether the low-temperature integrated time measured in the previous engine operation is equal to or larger than the predetermined comparative time includes determining whether the low-temperature integrated time stored in the memory is equal to or larger than the predetermined comparative time.

* * * * *